United States Patent [19]

Magdassi et al.

[11] Patent Number: 5,753,264
[45] Date of Patent: May 19, 1998

[54] METHOD OF MAKING POSITIVELY CHARGED MICROCAPSULES OF EMULSIONS OF OILS AND ITS USES

[75] Inventors: Shlomo Magdassi; Kosta Mumcuoglu, both of Jerusalem; Uri Bach, Efrat; Yulia Rosen, Jerusalem, all of Israel

[73] Assignee: Yissum Research Development Company of the Hebrew University, Jerusalem, Israel

[21] Appl. No.: 578,855

[22] Filed: Dec. 26, 1995

Related U.S. Application Data

[63] Continuation-in-part of Ser. No. 266,025, Jun. 27, 1994, Pat. No. 5,518,736.
[51] Int. Cl.$^6$ .............................. A61K 7/42; A61K 9/50; A61K 9/52; A61K 35/78
[52] U.S. Cl. .................. 424/451; 424/195.1; 424/455; 424/457; 424/489; 424/59; 514/938; 514/963; 514/975
[58] Field of Search .................. 424/451, 489, 424/455, 457, 59, 195.1; 514/938, 963, 975

[56] References Cited

U.S. PATENT DOCUMENTS 4,923,977  5/1990  Lang et al. ..................... 536/20

*Primary Examiner*—James M. Spear
*Attorney, Agent, or Firm*—William S. Frommer; Frommer Lawrence & Haug LLP

[57] ABSTRACT

The invention relates to a process for preparing a chitosan-containing microcapsules and emulsions of an oil including the steps of (a) forming an oil-in-water emulsion by homogenizing said oil into an aqueous solution containing an anionic emulsifier; and (b) adding to the emulsion obtained in (a) an aqueous chitosan solution while continuously homogenizing the mixture to give a stable emulsion, which is converted into microcapsules by using the proper electrolyte and pH changes. Also encompassed are preparations including as active ingredient a lice repelling agent, vitamin E or a UV radiation photoprotectant. The preparations may be sustained-release or long acting preparations.

33 Claims, 9 Drawing Sheets

METHOD OF MAKING POSITIVELY CHARGED MICROCAPSULES OF EMULSIONS OF OILS AND ITS USES

CROSS-REFERENCE TO RELATED APPLICATIONS

This application is a continuation-in-part of application Ser. No. 08/266,025 filed Jun. 27, 1994, now U.S. Pat. No. 5,518,736 which is incorporated herein by reference.

FIELD OF THE INVENTION

The invention relates to a method for the preparation of biodegradable, oil-containing emulsions and microcapsules. The emulsions and microcapsules are particularly useful as active ingredients in lice repelling and other, such as vitamin preparations and UV radiation photoprotectants, which are also encompassed by the invention.

BACKGROUND OF THE INVENTION

Formation of microcapsules, capsules or beads by chitosan was suggested for encapsulation of pharmaceuticals, enzymes, cells, etc. The reported procedures are based on:

A. Using a combination of chitosan, which is a polycationic substance, with a polyanionic substance such as gum Arabic, by a method known as complex coacervation (e.g. JP 87-173464). By this method, an insoluble polymeric shell is produced.

B. Formation of the microcapsules by dispersing an aqueous solution, which contains chitosan, in an oil phase, followed by gelling (e.g. JP 90-317739). This method is based on formation of a separate phase in oil, followed by gellification of the aqueous droplet, and not only the interface.

C. Covalent crosslinking of e.g. beads, by using special crosslinking agents, followed by UV irradiation (e.g. WO 87-US1495).

D. Formation of polymeric spheres by providing droplets of polyanion monomer solution, which meets a stream of polycation monomer solution (e.g. WO 92-US9781). This method is based on technology which allows specific contact points between the reactants, and the resulting particle size is controlled by the machinery.

E. Formation of beads, by emulsification of an oil phase directly into a chitosan solution, which is then dropwise added into a solution containing diphosphate and glyoxal hydrate, which leads to crosslinking (e.g. EP 543572). Here, there is no microencapsulation process which occurs at the oil-water interface, but a simple gellification of the whole bead.

As will be shown in the following description, the process of the invention is based on formation of an insoluble wall around each, or only few droplets, in such manner that this wall separates each oil droplet from the aqueous phase.

Adsorption of chitosan molecules onto negatively charged particles or emulsions is expected due to electrostatic -interactions, as shown by Faldt et al., Colloids and Surfaces A (1993) 71:187–195, for stable oil-in-water emulsions (prior to addition of chitosan). They found that chitosan leads to flocculation (aggregation) of the emulsion droplets, at high pH due to charge neutralization, a phenomena which should be avoided. Contrary to this publication, in the present invention the emulsification and microencapsulation process is performed in such a lecithin:chitosan weight ratio, and pH range, in which individual droplets can be coated with an insoluble layer of chitosan, without having flocculation. In addition, contrary to Faldt et al. wherein it is stated that "The ratio of phosphatydyl choline to sodium glycolic acid and the number of passes through the microfluidizer were chosen to obtain an emulsion of high stability", by the present invention unstable emulsions are used for the beginning of the microencapsulation and chitosan coating process.

Formation of biodegradable chitosan-containing aqueous emulsions or sustained release chitosan microcapsules, which have good adhering properties to negatively charged surfaces is desired, and would have a particular advantage for providing oil containing biodegradable long-acting lice repelling compositions and UV radiation photoprotectants.

The number of cases of human lice infestation throughout the world is estimated at hundreds of millions each year [Taplin, D. and T. L. Meinking, Sem. Dermatol. (1987) 6:125–135]. The conventional treatment for head lice consists of using synthetic ingredients, which are licidals. However, these chemicals do not solve the problem of reinfestation, which occurs frequently among children. Therefore, the need for a lice repellent is clear.

Insect repellents mostly operate from a distance by confusing the insect's direction finding mechanisms and close up by acting as sensory blockers [Wright, R. H., Sci. Amer. (1975) 233:104–111]. They render the host animal unattractive and in this way protect the host animal from the bites of insects, or ticks and the most pathogenic microorganisms which they transfer. Repellents are normally volatile and consequently remain on the user for a limited period of time.

In the past, lavender oil was used to protect children from head lice infestation [Burgess, I., Br. J. Dermatol. (1993$^a$) 128:357–358]. Recently piperonal (1,3-benzodioxol-5-carboxaldehyde) was introduced as a repellent to the market [Burgess, I., Pharmaceutical J. (1993$^b$) 15:674–675], however, it was shown earlier that this substance has also pediculicidal activity [Moore, W., JAMA (1918) 71:530–531].

The U.S. army has for a long time applied the following repellents to clothing, against body lice: M-1960 (30% 2-butyl-2-ethyl 1–3 propanediol, 30% benzyl benzoate, 30% n-butylacetanilidine and 10% Tween 80), 90% benzyl benzoate and a combination of 75% N,N-diethyl-m-toluamide (DEET) and 25% ethanol. Pyrethrum has been used to impregnate underwear, and has both a repellent and toxic effect [Eldridge, B. F., In: The control of lice and louseborne diseases (1973) PAHO/WHO Sci. Pub. No. 263, pp177–178].

Today the US and Australian armies are using permethrin and dibutylphthalate as a clothing treatment against a number of medically important arthropods, particularly mosquitoes and chiggers [Gibta, R. K. et al., J. Am. Mosq. Control Assn. (1987) 3:556–560; Frances, S. P. et al., J. Ned. Entomol. (1992) 29:907–910].

The repellent DEET, which is widely used against several arthropods of medical importance, exhibits several side-effects including cardiovascular effects, encephalopathies, allergic and psychotic reactions [Robbins, P. J. and M. G. Cherniak, J. Toxicol. Environ. Health (1986) 18:503; Edwards, D. L. and C. E. Johnson, Clin. Pharm. (1987) 6:496–498; Leach, G. J. et al., J. Toxicol. Environ. Health (1988) 25:217].

It is therefore clear why a natural lice repellent composition is required, especially if formulated in such a way that it would yield long duration of lice repellency.

Sustained release preparations of other oily active agents, such as vitamin E or oil-soluble UV radiation photoprotectants has also encountered problems. For example, the optical properties of photoprotectants are required while they stay on the skin. However, the contact between the skin and the photoprotectant is often a problem, due to the chemical composition of the protectant, which might cause allergenic effects, and in some cases also cause skin diseases.

SUMMARY OF THE INVENTION

The present invention relates to a process for preparing a positively charged chitosan-containing aqueous emulsion of an oil comprising the steps of (a) forming an oil-in-water emulsion by homogenizing said oil into an aqueous solution containing an anionic emulsifier; and (b) adding dropwise to the emulsion obtained in (a) an aqueous chitosan solution, in a weight ratio which favors precipitation of insoluble surfactant-chitosan complex, while continuously homogenizing the mixture to give a stable emulsion at low pH due to chitosan-surfactant insoluble complex formation.

The invention further relates to a process for preparation of positively charged microcapsules of oil droplets dispersed in an aqueous solution comprising the steps of (a) forming an oil-in-water emulsion, by homogenizing oil, water and an anionic emulsifier; (b) adding to the emulsion obtained in (a) an aqueous chitosan solution while continuously homogenizing the mixture to give a stable emulsion and optionally diluting this stable emulsion in water or a suitable aqueous solution; (c) adding to the emulsion obtained in (b) an agent capable of increasing the pH or a water soluble cross-linking electrolyte which is capable of increasing the pH of the solution and of cross-linking the chitosan polymeric chains, a pH of from about 5 to about 7.5 being maintained by adding a suitable agent, and stirring the mixture for a suitable period of time to give a dispersion of fine microcapsules in water; and (d) optionally removing the aqueous phase from the dispersion obtained in (c) to give a powder.

The invention further relates to a process for the microcapsulation of fine oil droplets dispersed in an aqueous solution comprising the steps of (a) forming an oil-in-water emulsion, by homogenizing oil, water and an anionic emulsifier (a negatively charged surfactant); (b) adding to the emulsion obtained in (a) an aqueous chitosan solution while continuously homogenizing the mixture; and (c) increasing the pH of the mixture obtained in (b) in order to cause precipitation of the chitosan on the oil droplets to form microcapsules (the pH should be below 7.5).

Chitosan is adsorbed to the negatively charged oil droplets to form an insoluble complex which is further solidified by pH increase or a cross-linking agent.

In the process according to the invention the formation of wall capsule is at the oil-water interface, thus microcapsules, and not beads, are obtained.

In addition, the invention relates to a sustained-release biodegradable lice repelling preparation comprising as active ingredient a lice repelling agent comprising at least one natural oil selected from the group consisting of citronella oil, rosemary oil and eucalyptus oil, or at least one natural oil component selected from the group consisting of citronella and geraniol or mixtures thereof; an anionic emulsifier; chitosan; and optionally further comprising dermatologically acceptable additives, carriers or diluents.

In particular embodiments the sustained-release biodegradable lice repelling preparations of the invention may be in the form of an aqueous emulsion or the active ingredient may be in the form of chitosan microcapsules.

The particular embodiments of the sustained-release lice repelling preparations of the invention may be prepared by the process of the invention.

Further, the invention relates to preparations comprising as active ingredient vitamin E or a UV radiation photoprotectant; an anionic emulsifier; chitosan; and optionally further comprising pharmaceutically acceptable additives, carriers or diluents. The preparations may be sustained-release preparations.

DETAILED DESCRIPTION OF THE INVENTION

Figure 1:
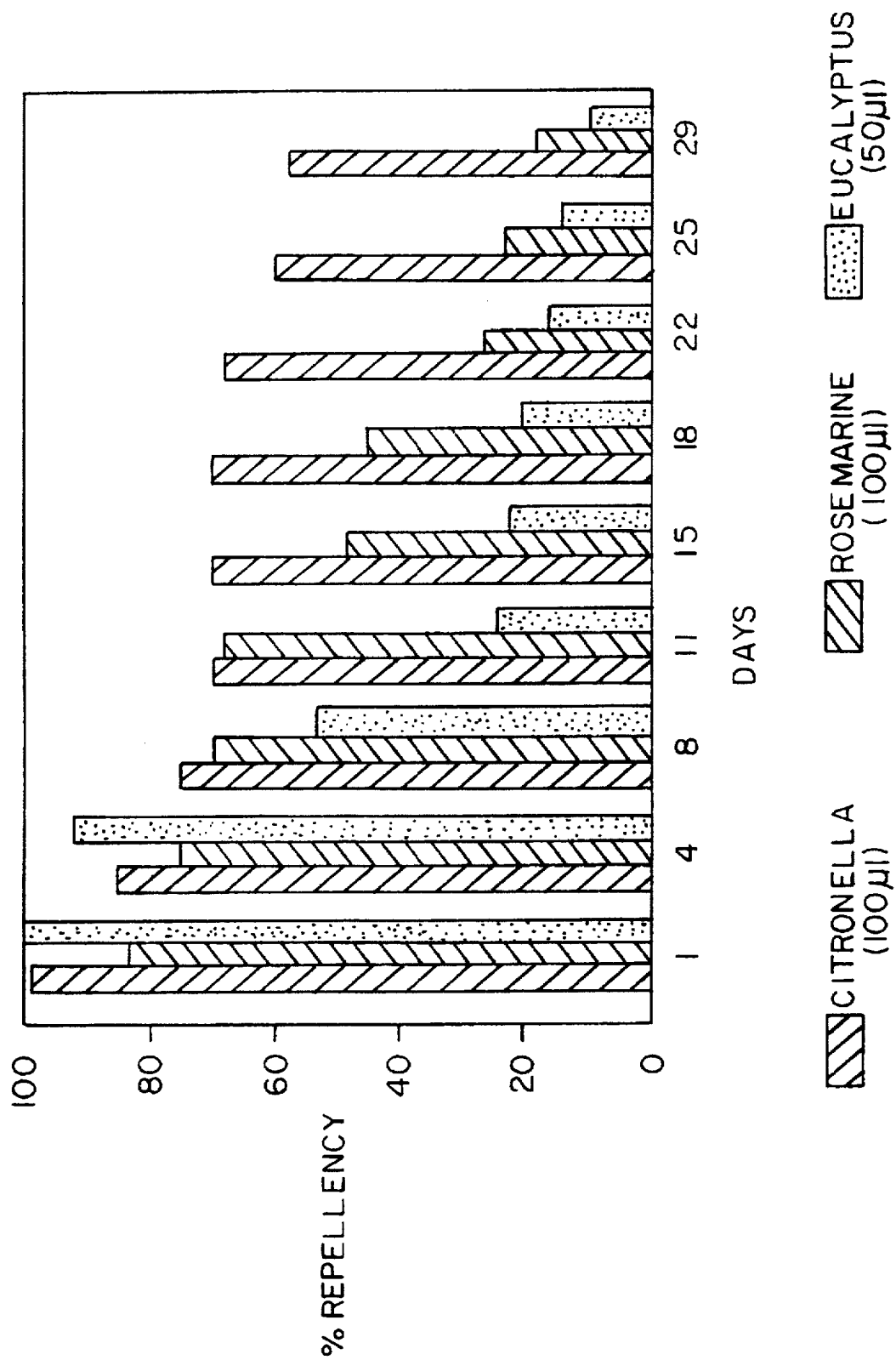
FIG. 1 illustrates the lice repellent effect of citronella, rosemary and eucalyptus oils.

In a first embodiment, the invention relates to a process for preparing a positively charged chitosan-containing aqueous emulsion of an oil comprising the steps of (a) forming an oil-in-water emulsion by homogenizing said oil into an aqueous solution containing an anionic emulsifier; and (b) adding dropwise to the emulsion obtained in (a) an aqueous chitosan solution, in a weight ratio which favors precipitation of insoluble surfactant-chitosan complex, while continuously homogenizing the mixture to give a stable emulsion at low pH due to surfactant-chitosan complex formation.

In a second embodiment, the invention relates to a process for preparation of positively charged microcapsules of oil droplets dispersed in an aqueous solution comprising the steps of (a) forming an oil-in-water emulsion, by homogenizing oil, water and an anionic emulsifier; (b) adding to the emulsion obtained in (a) an aqueous chitosan solution while continuously homogenizing the mixture to give a stable emulsion and optionally diluting this stable emulsion in water or a suitable aqueous solution; (c) adding to the emulsion obtained in (b) an agent capable of increasing the pH or a water soluble cross-linking electrolyte which is capable of increasing the pH of the solution and of cross-linking the chitosan polymeric chains, a pH of from about 5 to about 7.5 being maintained by adding a suitable agent, and stirring the mixture for a suitable period of time to give a dispersion of fine microcapsules in water; and (d) optionally removing the aqueous phase from the dispersion obtained in (c) to give a powder.

In a third embodiment, the invention relates to a process for the microcapsulation of fine oil droplets dispersed in an aqueous solution comprising the steps of (a) forming an oil-in-water emulsion, by homogenizing oil, water and an anionic emulsifier (a negatively charged surfactant); (b) adding to the emulsion obtained in (a) an aqueous chitosan solution while continuously homogenizing the mixture; and (c) increasing the pH of the mixture obtained in (b) in order to cause precipitation of the chitosan on the oil droplets to form microcapsules.

In the processes of the invention said oil can be a natural oil, a synthetic oil, a natural oil component, soybean oil, vitamin E, oil-soluble UV radiation photoprotectants, D-limonen, a fruit extract or a flavoring extract or a mixture thereof.

For preparing the lice repelling preparations of the invention said oil is a natural oil, preferably rosemary oil, citronella oil, or eucalyptus oil or a mixture thereof, or a natural oil component, preferably citronellal or geraniol or a mixture thereof, or mixtures of these natural oils and natural oil components.

For preparing UV radiation photoprotectant preparations of the invention said oil may be octyl methoxy cinnamate.

The anionic emulsifier can be sodium dodecyl sulphate, a phospholipid or a mixture of phospholipids such as lecithin, or a soap, such as sodium, potassium or ammonium stearate, oleate or palmitate. Lecithin is a preferred emulsifier.

In the processes of the invention the pH of the chitosan solution employed in step (b) is about 1–2.5 and the final pH of the stable emulsion obtained is about 3.5. The pH can be adjusted by any suitable acid, for example 10% citric acid or 10% acetic.

In the process according to the second embodiment, the cross-linking electrolyte is a water soluble polyphosphate, such as tripolyphosphate, preferably sodium or potassium tripolyphosphate. In step (c) of this process, the acid employed is preferably an organic acid, such a citric, lactic, acetic or fumaric acid and said suitable period of time is from 2 to 6 hours. In step (d) of this process, the aqueous phase can be removed from the dispersion obtained in step (c) by lyophilization, spray-drying or oven vacuum drying at a suitable temperature.

In each embodiment, the process according to the invention may further comprise, after step (b), the addition of a dispersing agent which may be an anionic or cationic surfactant. For example, sodium dodecyl sulphate (SDS) or CTAB may be employed. The addition of the surfactant prevents agglomeration of particles during said step (c).

The invention also relates to sustained-release biodegradable lice repelling preparations comprising, as active ingredient, a lice repelling agent comprising at least one natural oil selected from the group consisting of citronella oil, rosemary oil and eucalyptus oil, or at least one natural oil component selected from the group consisting of citronellal and geraniol or mixtures thereof; an anionic emulsifier; chitosan; and optionally further comprising dermatologically acceptable additives, carriers or diluents.

The sustained-release biodegradable lice repelling preparation may be in the form of an aqueous emulsion of said oil. The anionic emulsifier is a phospholipid or a mixture of phospholipids, lecithin being preferred.

In a preferred embodiment, sustained release biodegradable lice repelling composition according to the invention, in the form of an oil-in-water emulsion, is prepared by the process according to said first embodiment of the invention.

Alternatively, the active ingredient in the lice repelling biodegradable preparation according to the invention may be present in the form of chitosan microcapsules. Preferably, the chitosan microcapsules are prepared by the process according to said second embodiment of the invention.

In both the emulsion form and chitosan microcapsules form, said active lice repelling natural oil is preferably citronella and said active lice repelling natural oil component is geraniol. The lice repelling preparations of the invention may of course contain a mixture of the active natural oil and natural oil components.

The invention further relates to UV radiation photoprotectant preparations comprising at least one oil, such as octyl methoxy cinnamate; an anionic emulsifier; chitosan; and optionally further comprising dermatologically acceptable additives, carriers or diluents. The oil may also be a UV radiation photoprotectant, such as oxybenzon, dissolved in oil.

The preparation may be in the form of an aqueous emulsion or dispersion of microcapsules of said oil. The anionic emulsifier is a phospholipid or a mixture of phospholipids, lecithin being preferred.

In a preferred embodiment, the UV radiation photoprotectant composition according to the invention is prepared by the process according to said third embodiment of the invention.

Alternatively, the dispersion can be lyophilized to remove the water, thus forming a powder of microcapsules during the process of water removal, several additives can be added (such as PEG, surfactants), to allow easy re-dispersion.

The positive charge should enhance the adhesion of the microcapsules to a negatively charged surface, such as hair and skin. It should allow attachment of the octyl methoxy cinnamate oil (the UV protectant), to stay on the skin, without direct contact, an advantage over the currently used UV protective emulsions. The oil, also, cannot penetrate through the skin.

The oil droplets will absorb the UV light, and in addition, the polymeric shell of the chitosan around the droplets will reflect the light, so that a combined effect is achieved.

The following Examples describe the preparation of oil-in-water emulsion, and of microcapsules in water dispersion for rosemary oil. It is well within the capabilities of the man skilled in the art to use other oils or oil components in a similar manner.

In principle, the process of the invention is based on the following steps:

Formation of oil-in-water emulsion, by using an anionic emulsifier such as, e.g., lecithin; and Addition of chitosan solution at low pH to the above emulsion, while continuously homogenizing. In this step, a stable emulsion, preferably at pH=3.5 is obtained. This pH is strongly dependent on the type of acid used to dissolve the chitosan.

The emulsion obtained may then be diluted in distilled water.

In the process for preparing chitosan microcapsules the thus obtained stable emulsion, which preferably has been diluted, is subjected to the following:

Dropwise addition of sodium tripolyphosphate solution into the above diluted emulsion, while the pH is kept constant at 5.3. In this step a dispersion of fine microcapsules in water is obtained. The required pH is strongly dependent on the type of acid used to dissolve the chitosan.

At the end of the process a dispersion of microcapsules in water is obtained. It is possible to obtain microcapsules powder, simply by lyophilization or drying in fluidized bed of the above dispersion.

In the above process/es an emulsion is formed by an emulsifier, which is capable of interacting with chitosan. In prior art processes employing chitosan, e.g. EP-A-543572, core material is added into the hardening agent solution. This difference allows formation of fine microcapsules, compared to large beads, which are obtained by the other processes. Needless to say, large beads would not be suitable for the purposes of the preparations of the invention.

Figure 6:
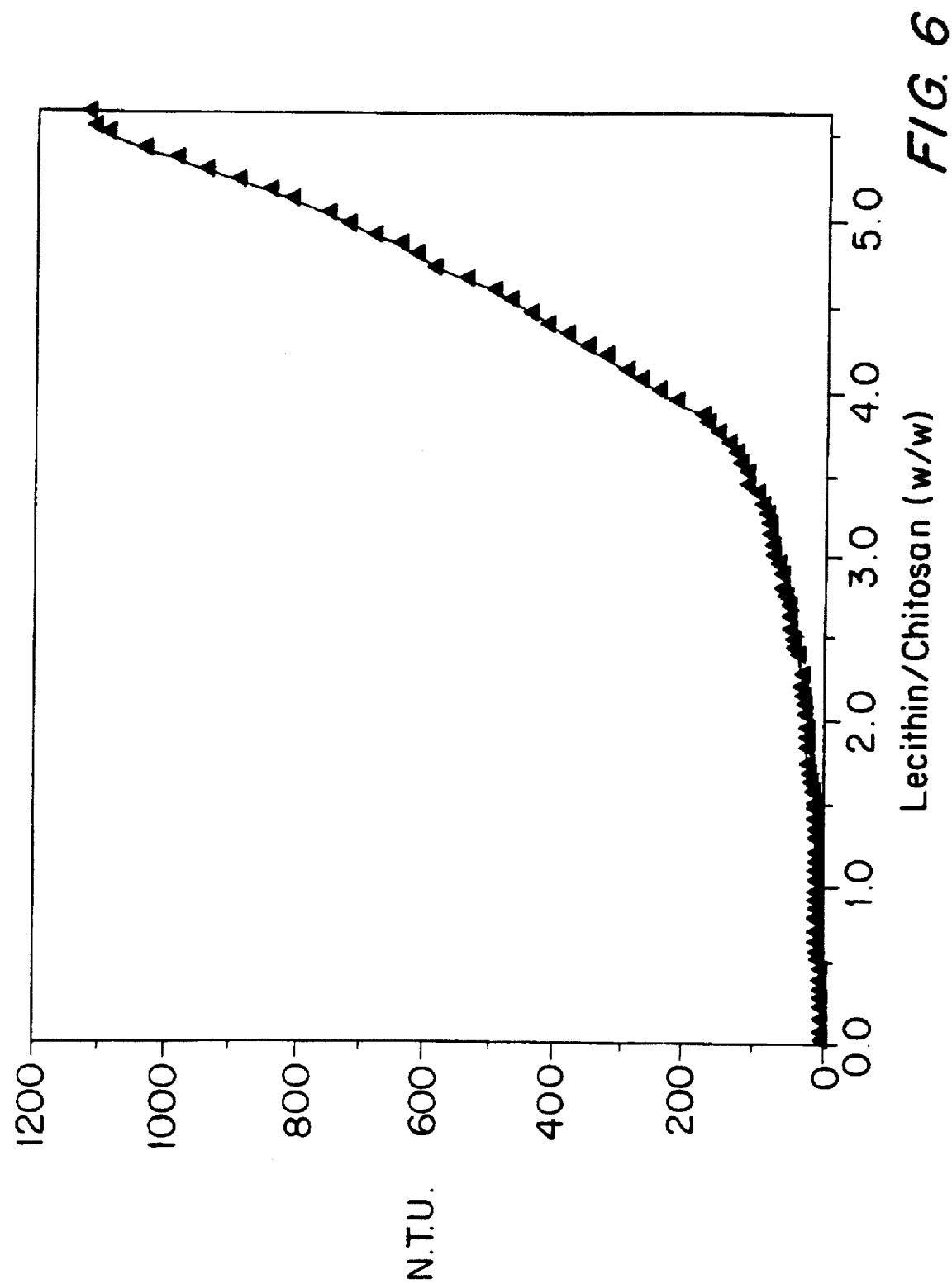
FIG. 6 shows turbidity (in universal nephlometric units) of chitosan solutions, after addition of lecithin at various lecithin-chitosan weight ratios (in citric acid)

The encapsulation concept is based on formation of an insoluble surfactant-chitosan complex at the oil-water interface. It is found that this precipitation occurs only above a specific weight ratio of lecithin to chitosan, as shown in FIG. 6, by turbidity measurements. Furthermore, it is found that the favorable pH for having such precipitation is strongly dependent on the type of acid which is used or the initial dissolving of the chitosan. For citric acid, this pH is around 3.5.

The lice repelling preparations of the invention can be applied to the hair as such or they can be admixed with hair shampoos or conditioning preparations.

Figure 5:
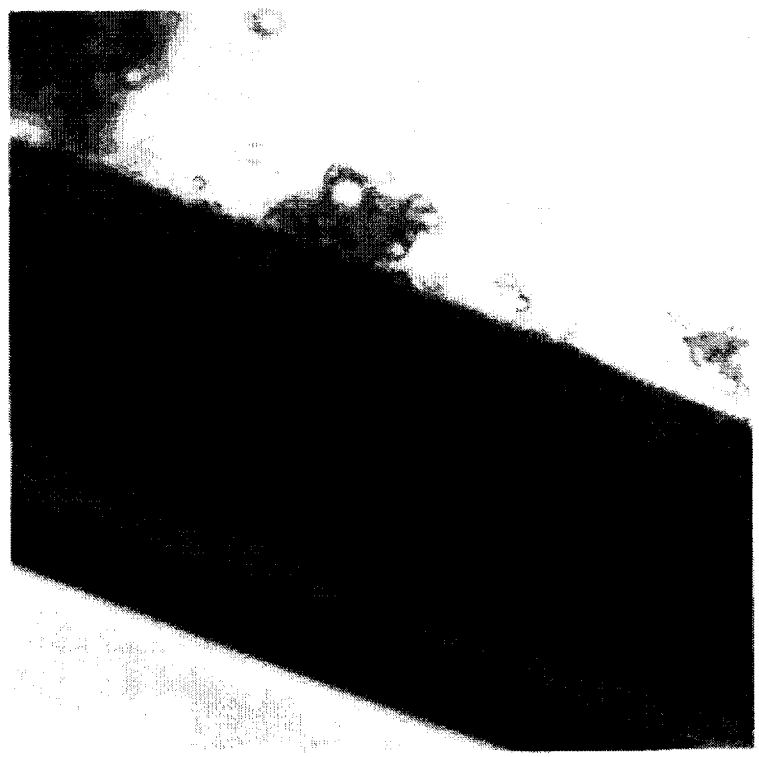
FIG. 5 shows the adhesion of chitosan coated emulsion droplets (microcapsules) onto hair fibers (magnification× 400)

One of the remarkable properties of the chitosan-containing oil-in-water emulsions and the chitosan microcapsules of the invention is the ability of the droplets, in the emulsion, or the microcapsules to adhere onto hair fibers, which are generally negatively charged. This adherence is demonstrated in FIG. 5.

This property is of great significance to the present invention, since the active lice repelling oils or oil components will adhere to the hair, and thereafter will be slowly released, leading to a biodegradable sustained release formulation.

The chitosan microcapsules containing lice repelling preparations of the invention can also be adhered to suitable carrying means, such as decorative tapes, hairpins or earrings, to be worn by the user.

In yet another embodiment, the invention relates to sustained release or long acting preparations comprising as active ingredient vitamin E or a UV radiation photoprotectant; an anionic emulsifier; chitosan; and optionally further comprising pharmaceutically acceptable additive, carriers or diluents.

The vitamin E may be in any biologically compatible form of α-tocopherol, or mixtures of different compatible forms.

UV radiation photoprotectants may be, for example, octyl methoxy cinnamate.

In these preparations the active ingredient may be present in the form of an aqueous emulsion, which is preferably prepared by said first embodiment of the process of the invention, or in the form of chitosan microcapsules, preferably prepared by said second or third embodiment of the process of the invention.

EXAMPLES

Material and Methods

Lice—The human body louse, nediculus humanus humanus, was reared by feeding the lice every 48 hours on rabbits. Lice were placed on the shaved abdomen of white New Zealand rabbits and left until fed to satiety. Outside the host, the lice were maintained at a temperature of 30° C. and relative humidity of 70–80%. For each test, 20 female lice, which had been fed 24 hrs before, were used.

Chemicals—The natural oils citronella, rosemary, eucalyptus, lavender and D-limonen and essential oils components such as citronellal, geraniol, linalool, bornyl acetate, camphor, cineol, pinene, camphene and borneol were used. Absolute ethanol served as negative control and DEET as positive control.

Bioassay—The petri-dish method was used to examine the repellency of the oil, oil components and control solutions employed. Whatman 4 filter paper discs (5.5 cm in diameter) were placed on petri-dishes. A 100 ml drop of the test solution was placed on a corduroy patch (1.5 $cm^2$). The material was allowed to dry in an incubator at 35° C. and 85–90% relative humidity. Control patches were treated in the same manner. The patches were placed at the periphery of the filter paper at a maximum distance apart from each other. Twenty female lice were placed in the middle of the filter paper and the petri-dish together with the lice were covered with a dark box in order to avoid any influence of light. The number of lice found on the treated and control patches, as well as on the area between the patches, were recorded after 10 min. Each component was tested three times. The duration of repellency was examined by testing the treated patches every 3–4 days. The concentration at which a given substance was still active was examined by preparing serial dilutions and examining the effect one day after treatment of the patches.

Calculations—The repellency was calculated according to the following equation:

$$\% \text{ Repellency} = [(\frac{1}{2}A - n)/\frac{1}{2}A] \times 100$$

where A=total number of lice n=number of lice found in the treated patch.

According to this equation, when lice were evenly distributed between the treated and untreated patches (n=½A), % repellency is equal to zero, and when no lice are left in the treated patch (n=0), the repellency is 100%.

Lice Repellency of Natural Oils and Natural Oil Components

Using the above evaluation methods, 14 oils and oil components were tested. The various oil components were tested in their crude form, without purification or special formulation. Results are summarized in Table 1. As shown in Table 1, out of 14 oils and oil components only five samples gave long repellent activity (above 1 week). These are citronella oil, rosemary oil and eucalyptus oil, and the specific active oil components are geraniol and citronellal.

TABLE 1

The Duration of Repellent Activity of Natural Oils and their Ingredients

| Compound | Activity of days |
|---|---|
| citronella | >29 |
| rosemary | >18 |
| eucalyptus | >8 |
| lavender | >1 |
| D-limonen | <1 |
| citronellal | >15 |
| geraniol | >8 |
| linalool | >1 |
| bornyl acetat | >1 |
| camphor | >1 |
| cineol | <1 |
| pinene | <1 |
| camphene | <1 |
| borneol | <1 |
| citronella emulsion | <8 |
| rosemary emulsion | >8 |

The duration of the repellent activity is demonstrated in FIG. 1, in which the repellency test results are presented at various time intervals. It can be clearly seen that up to 11 days the rosemary and citronella oils have very high and similar activities, while the rosemary oil continues to be effective for as long as one month.

Figure 2:
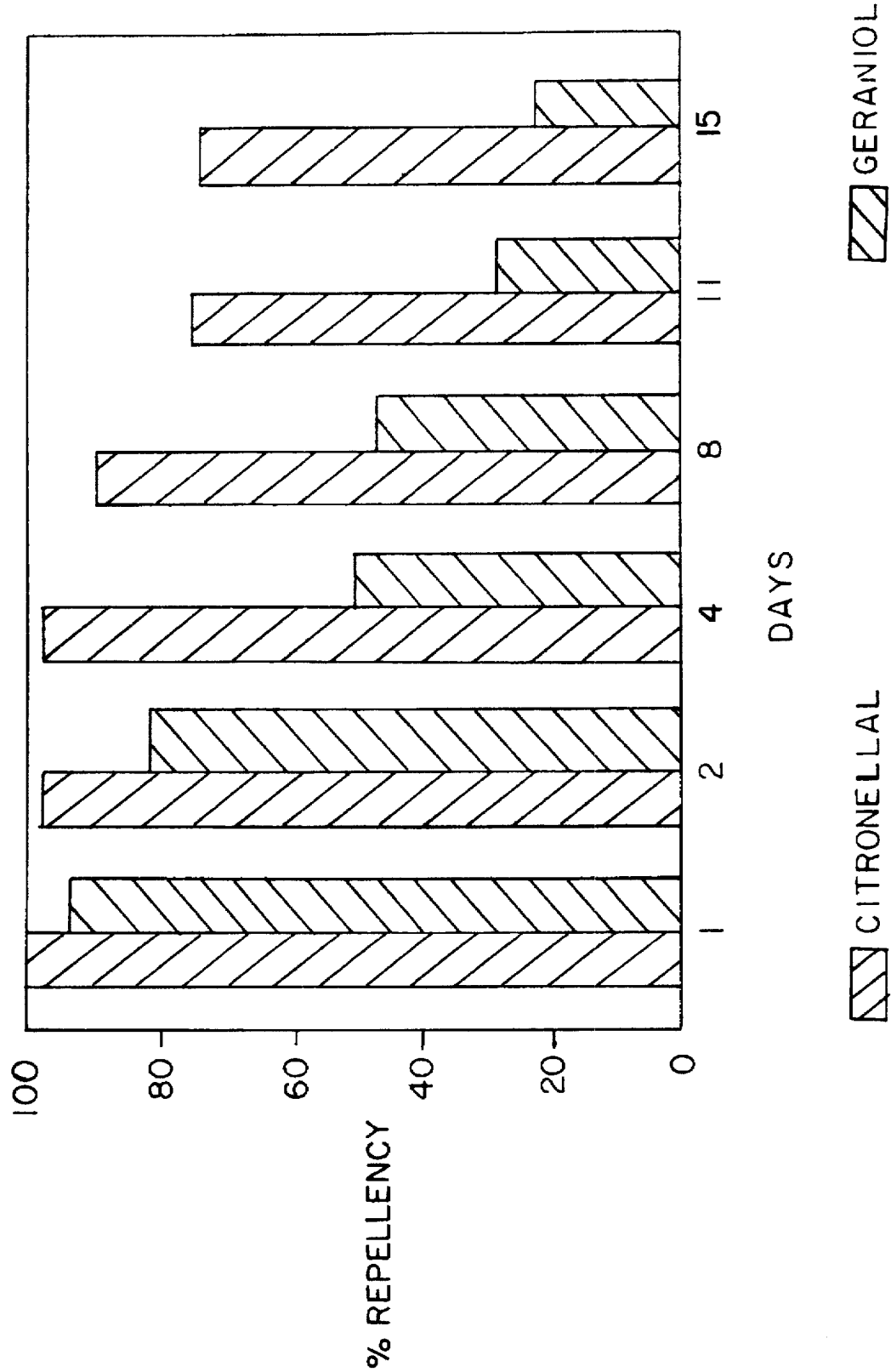
FIG. 2 illustrates the lice repellent effect of citronellal and geraniol.

A similar test was conducted for the individual oil components. As shown in FIG. 2, both citronellal and geraniol have the ability to repel lice, while citronellal has a longer activity duration.

Figure 3:
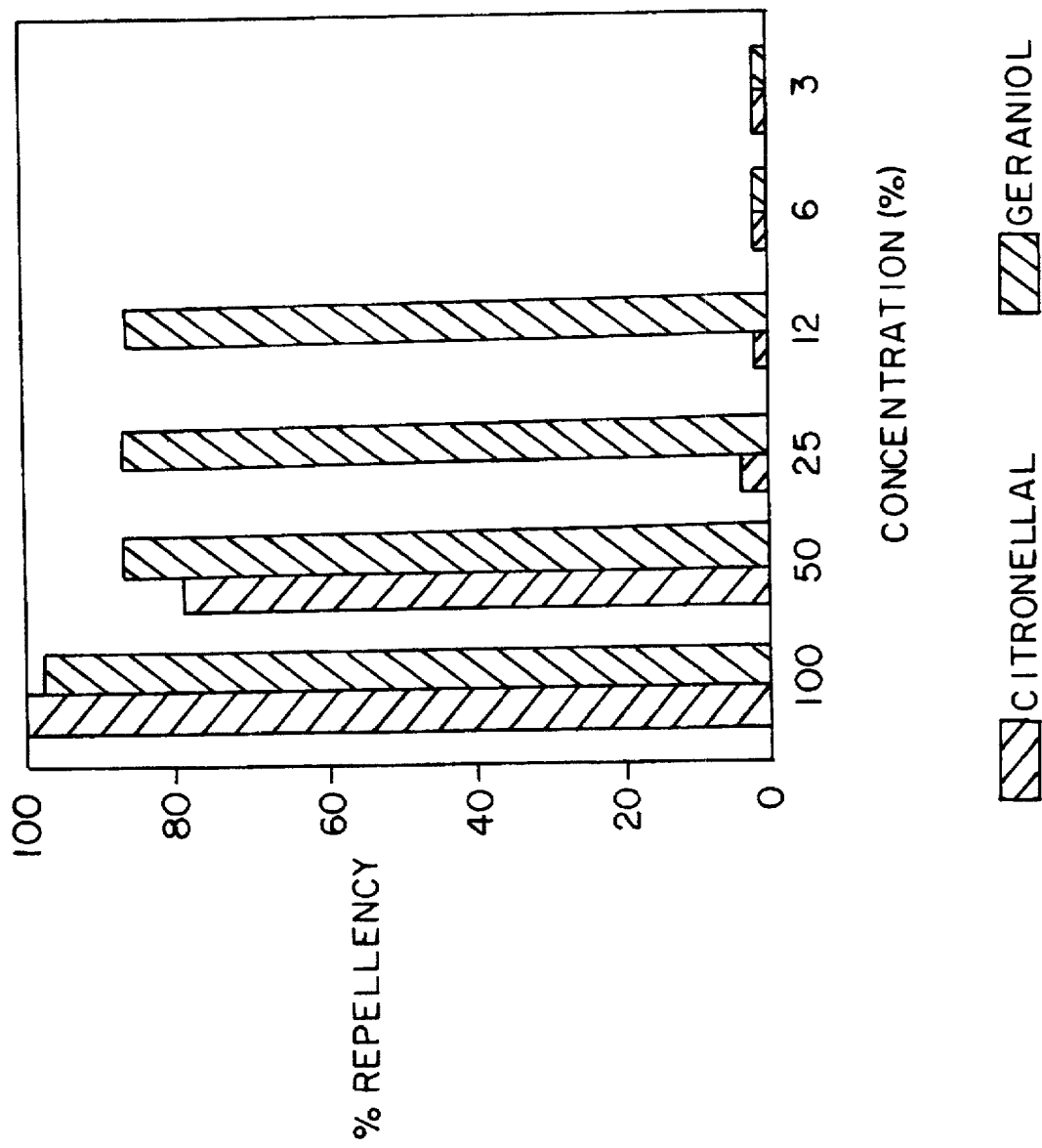
FIG. 3 illustrates the lice repellent effectiveness of various doses of geraniol and citronellal (expressed as % pure component)

These results show that the specific ingredients and three oils can be effective lice repellents. Although the duration of citronellal is longer than that of geraniol, geraniol is still effective at concentrations as low as 12% of the original dose, as shown in FIG. 3.

Lice Repellency of Natural Oils and Natural Oil Components in Aqueous Emulsions

Using the same procedure, the repellency of oil-in-water emulsions, which contained 30% w/w rosemary oil or citronella oil was tested. (The detailed description of emulsion formulation is given hereunder).

Figure 4:
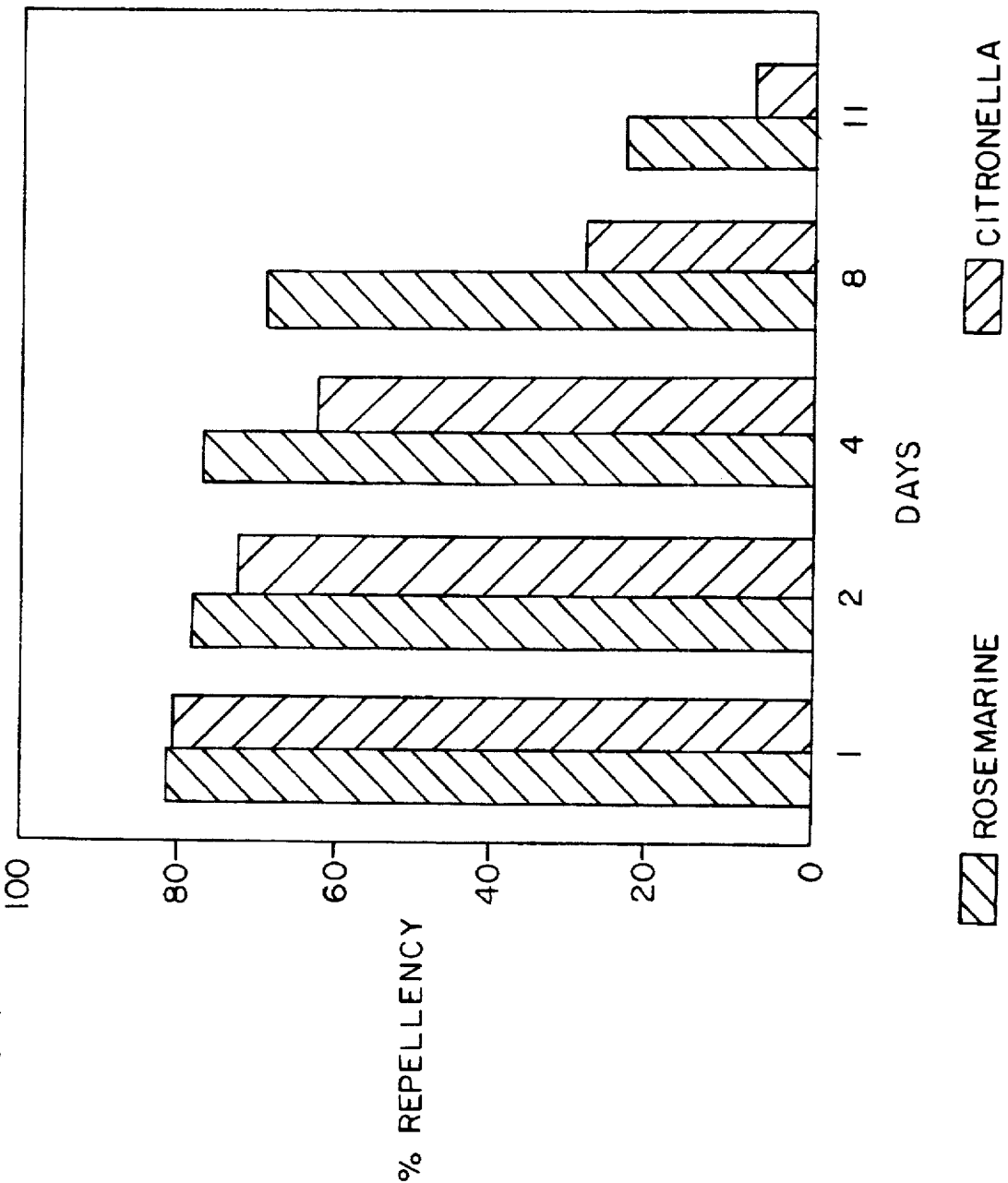
FIG. 4 illustrates the lice repellent effect of rosemary or citronella oil-in-water emulsions prepared with lecithin and chitosan.

As shown in FIG. 4, both emulsions have a long lasting activity: more than 60% repellency, after 4 days for both oils, and 8 days for the rosemary oil in water emulsion. It is obvious that these emulsions can be easily applied directly to the hair, either in liquid form or by spraying onto the hair.

Preparation of Emulsion

30% w/w rosemary oil were dropwise added into a 1% w/w lecithin (centrolex $p^R$) solution in water, while continuously homogenizing the system by a homogenizer. The lecithin solution was brought to pH=4.5 by citric acid, prior to addition of the oil phase. The homogenization was continued for 20 min, after which a white emulsion with a average droplet diameter of 2 μm was obtained while the droplets were negatively charged. A 2% w/w chitosan solution was separately prepared by dissolving chitosan into a 10% w/w citric acid solution. During the next step, the chitosan solution was dropwise added to the emulsion, while homogenizing, for 20 min. The volume of the added chitosan solution was half the volume of the emulsion.

The final composition of the emulsion was:

| | |
|---|---|
| rosemary oil | 15% w/w |
| chitosan | 0.5% w/w |
| citric acid | 5% w/w |
| lecithin | 0.35% w/w |
| $H_2O$ | 79.15% w/w |

The final pH of the emulsion was 3.5. This emulsion is stable for at least 8 months at room temperature.

Using this formulation, the lice repellency of two emulsions was tested: rosemary oil and citronella oil. It was found that both emulsions had a lice repelling activity, as shown in FIG. 3. Since only 15% of the emulsion sample is the oil phase, the repellency results are very impressive: only 15 μl of the oil (compared to 100 μl, FIG. 1) are capable of repelling lice for about one week. These results demonstrate the unique property of these emulsions, which is the slow release of the active ingredients.

Adhesion to hair fibers

Chitosan microcapsules containing rosemary oil were applied to human hair fibers by dipping the hair into the dispersion. As demonstrated in FIG. 5, the microcapsules adhered to the hair fiber. Therefore, it is expected that the rosemary oil will be slowly released at the vicinity of the hair fiber, repelling the lice.

Microencapsulation

The microencapsulation process is based on formation of an insoluble layer of chitosan, around the emulsion droplets.

The following is a representative example. 1. 20 ml of the above emulsion are mixed with 50 ml distilled water, while stirring at low speed. 2. 100 ml of sodium tripolyphosphate (STPP) solution (4% w/w) are added dropwise to the above diluted emulsion, with continuous stirring at low speed for about 4 hrs. The pH is maintained constant at 5.3, with the aid of suitable addition of citric acid solution.

At the end of the process a dispersion of microcapsules in water is obtained. It is possible to obtain microcapsules powder, simply by lyophilization or drying in fluidized bed of the above dispersion.

Preparation of Vitamin E Microcapsules

A 1% lecithine (Centrolex$^R$, which is stored under freezing) was prepared by dissolution in water. After the licithine is dissolved, the pH of the solution is adjusted to pH 4.5 by adding citric acid.

A 30% emulsion of vitamin E is prepared by adding the oily vitamin into the lecithine solution, while constantly homogenizing for about 20 min. until a yellow homogenous emulsion is obtained.

A 2% (w/w) chitosan solution is prepared by introducing the required quantity of chitosan into 10% citric acid. The mixture is stirred for about 2 hrs. and filtered through a stainless steel sieve to remove contaminations which were present in the chitosan.

The chitosan solution is then slowly added into the vitamin E emulsion at a 1:1 ratio, while constantly homogenizing for about 30 min.

The microcapsules are solidified by adding a 5% NaOH solution to the above emulsion until a pH of about 6 is obtained. At this stage the microcapsules float and can be easily filtered off and dried. Final drying is performed by lyophilizing for 24 hrs.

Preparation of UV Radiation Photoprotectant Microcapsules

A 1% lecithin solution (commercial, contains various components), at a pH of 4.5 (by lactic acid), was homogenized by a high speed homogenizer with the UV protectant, octyl methoxy cinnamate (speed=9000 RPM, time=10 minutes). The emulsion contained 30% w/w oil, the droplets were negatively charged (zeta potential=−38 mv), and the droplet size was 4.7 μm.

A 2% w/w chitosan solution was prepared by dissolving the chitosan in 1% w/w lactic acid solution. The final pH was about 4. The chitosan solution was dropwise added to the emulsion, while homogenizing for 20 minutes, at 5° C. The volume of chitosan solution added was equal to the volume of the emulsion. A white system was obtained, the droplet size was 5.3 μm, having a positive charge (zeta potential= +39.3 mv). This was a transition state between emulsion and microcapsule.

0.1% w/w NaOH was dropwise added to the above system, while stirring at low speed, until a pH of 6.2 was obtained. At this stage, a dispersion of positively charged microcapsules, in water, was obtained (zeta potential=+ 26.8).

Figure 7:
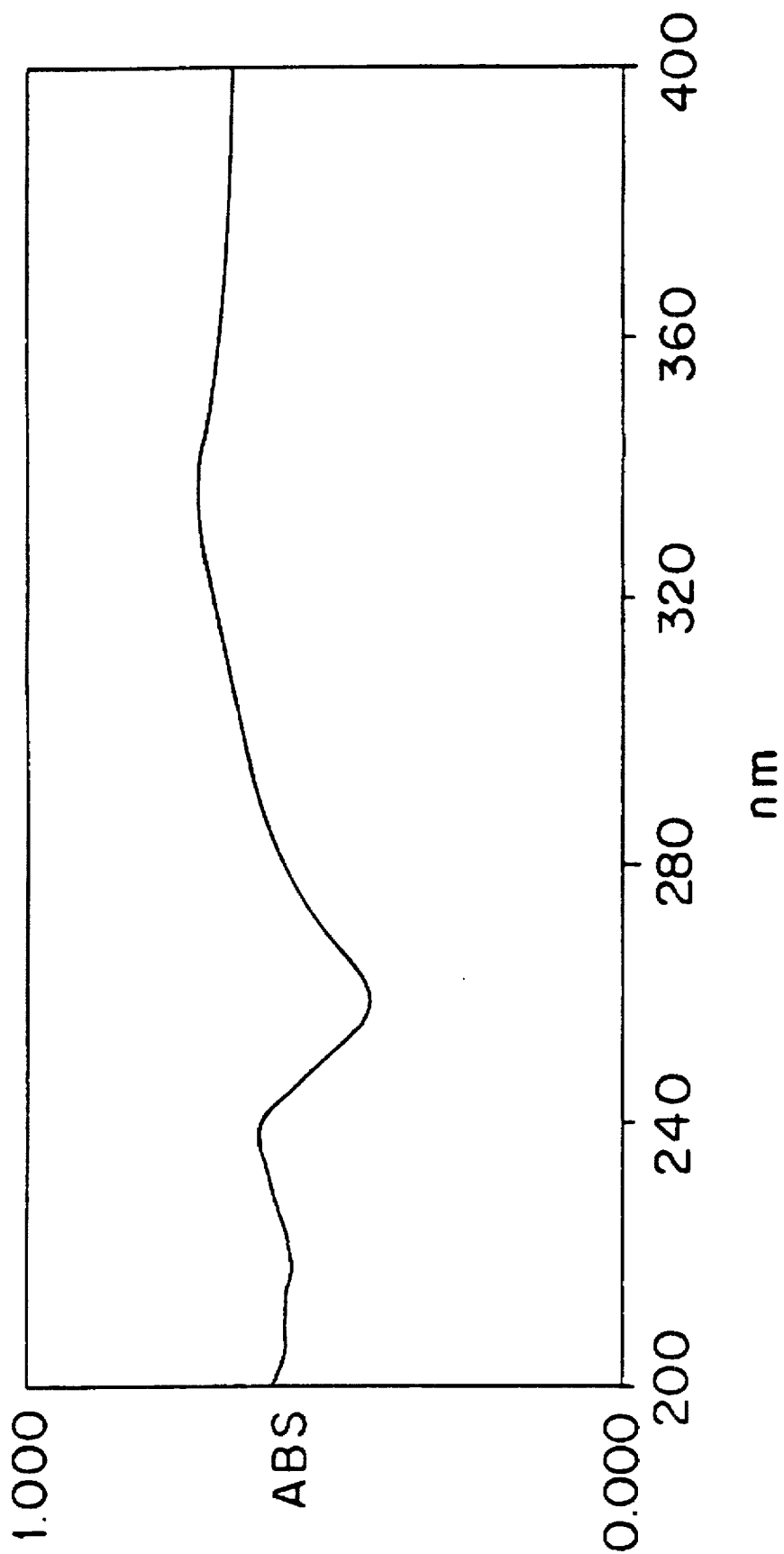
FIG. 7 shows the UV spectrum of a dispersion of microcapsules (1:1000 dilution) according to the invention wherein the oil is octyl methoxy cinnamate.

FIG. 7 shows the UV spectrum of the microcapsules, showing that the baseline is very high, as results from turbidity of the dispersion of microcapsules. This indicates the reflection of light. In addition, there is a peak around 320 nm indicating absorption.

Figure 8:
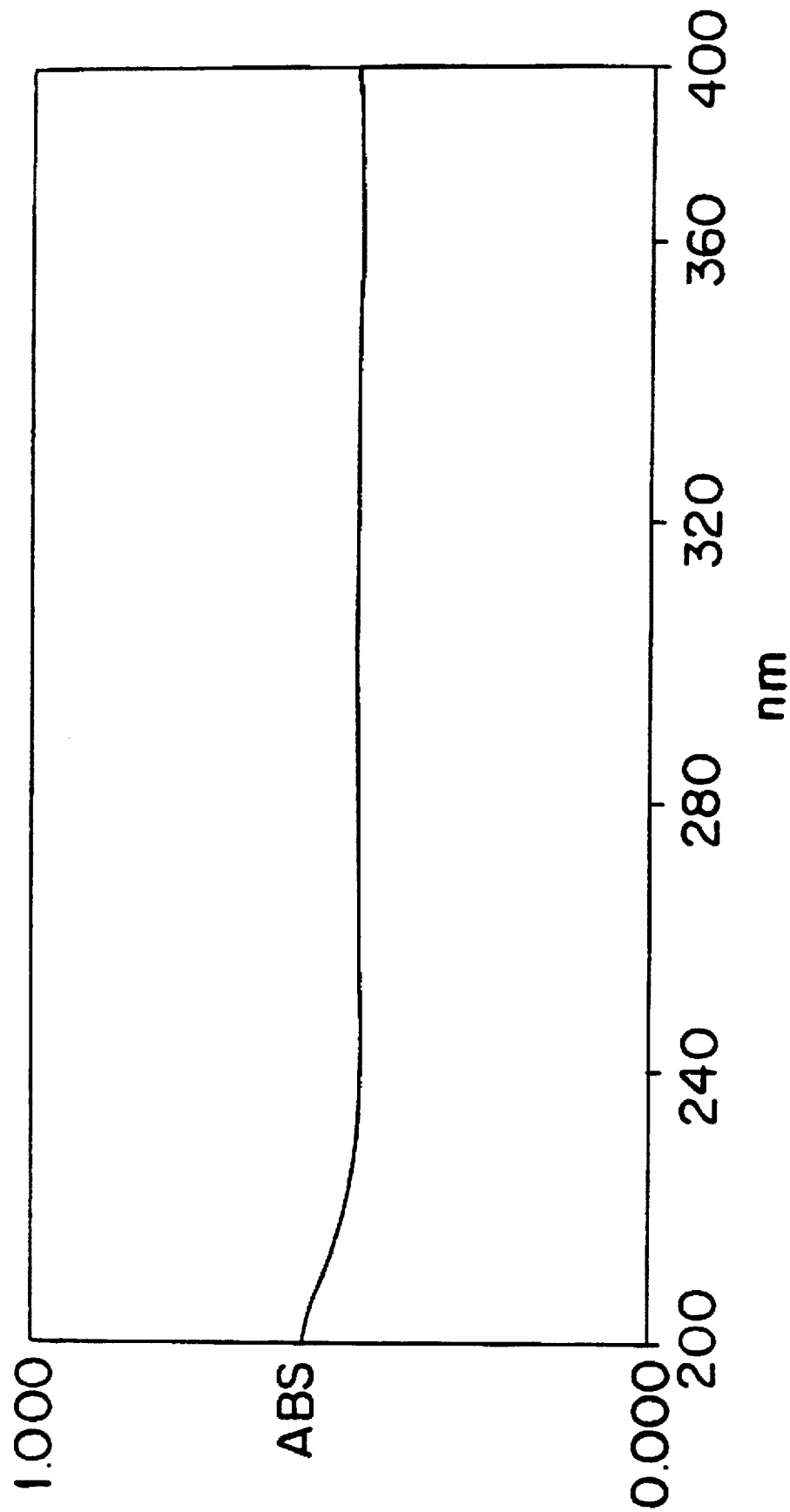
FIG. 8 shows the UV spectrum of a dispersion of microcapsules (1:1000 dilution) according to the invention wherein the oil is paraffin oil.

FIG. 8 shows turbidity of microcapsules of simple paraffin oil without the ability to absorb light.

Figure 9:
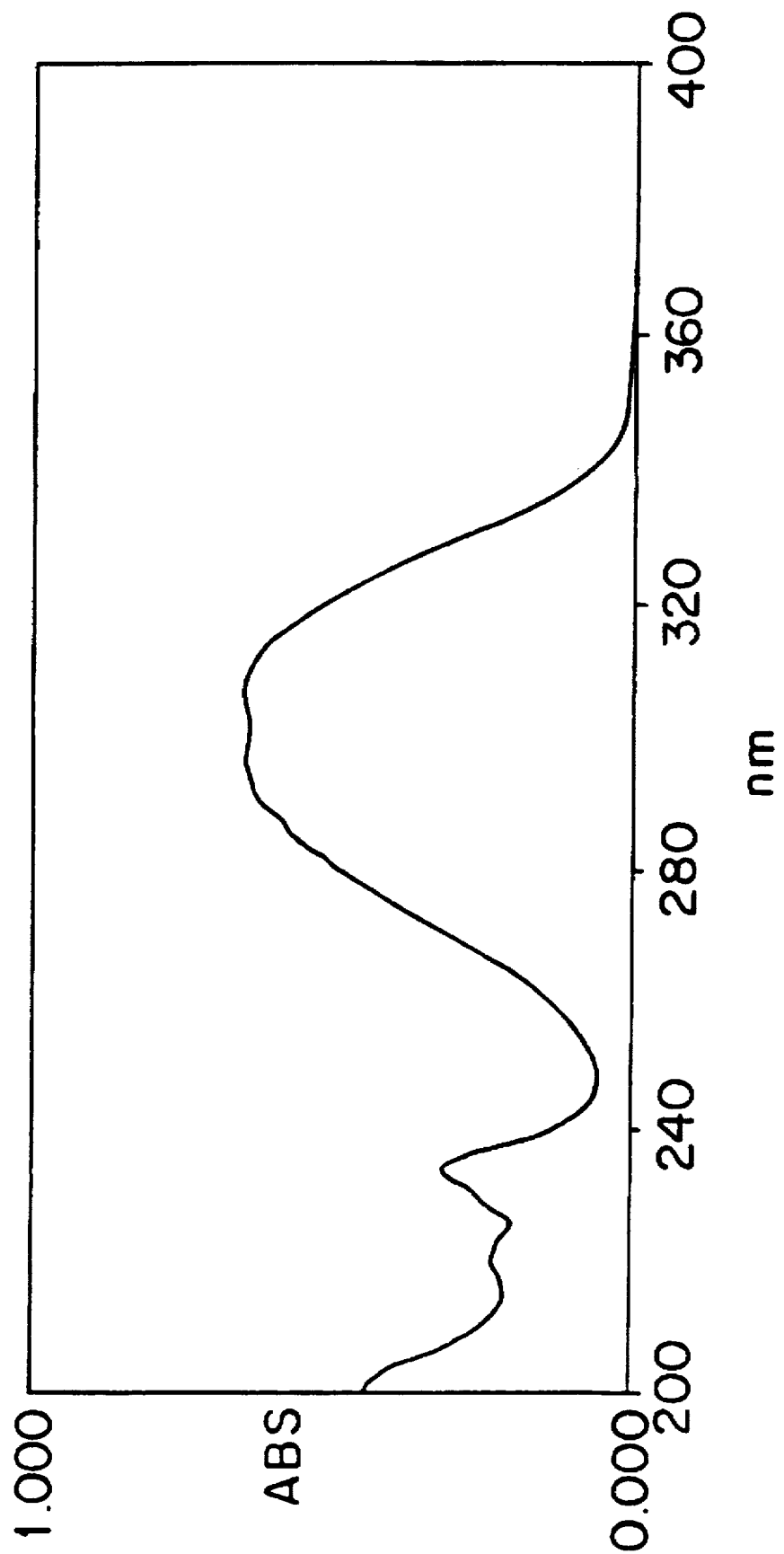
FIG. 9 shows the UV spectrum of a dispersion of microcapsules (1:100 dilution) according to the invention dried on a film after 24 hours.

FIG. 9 shows the UV absorption, at a dispersion of the microcapsules prepared according to the example, after it was diluted 1:100, and allowed to dry on a film. It is clear that the UV protection is maintained, even after the dispersion of microcapsules is dried. This experiment mimics the performance on the skin 24 hrs. after the microcapsules were applied to the film.

We claim:

1. A process for preparing a positively charged chitosan-containing aqueous emulsion of an oil comprising the steps of:
   (a) forming an oil-in-water emulsion by homogenizing said oil into an aqueous solution containing an anionic emulsifier; and
   (b) adding dropwise to the emulsion obtained in (a) an aqueous chitosan solution, in a weight ratio which favors precipitation of insoluble surfactant-chitosan complex, while continuously homogenizing the mixture to give a stable emulsion an acidic pH.

2. A process for preparation of positively charged microcapsules of oil droplets dispersed in an aqueous solution comprising the steps of:
   (a) forming an oil-in-water emulsion, by homogenizing oil, water and an anionic emulsifier;
   (b) adding to the emulsion obtained in (a) an aqueous chitosan solution while continuously homogenizing the mixture to give a stable emulsion and optionally diluting this stable emulsion in water or a suitable aqueous solution;
   (c) adding to the emulsion obtained in (b) a first agent capable of increasing the pH or a water soluble cross-linking electrolyte which is capable of increasing the pH of the solution and of cross-linking the chitosan polymeric chains, a pH of from about 5 to 7.5 being maintained, if necessary, by adding a suitable second agent, and stirring the mixture for a suitable period of time to give a dispersion of fine microcapsules in water; and
   (d) optionally removing the aqueous phase from the dispersion obtained in (c) to give a powder.

3. A process according to claim 1, wherein said oil is a natural oil, a synthetic oil, a natural oil component, soybean oil, vitamin E, UV radiation photoprotectants, D-limonen, a fruit extract or a flavoring extract or a mixture thereof.

4. A process according to claim 3 wherein said natural oil is rosemary oil, citronella oil, or eucalyptus oil or a mixture thereof.

5. A process according to claim 3 wherein said natural oil component is citronella or geraniol or a mixture thereof.

6. A process according to claim 1 wherein said anionic emulsifier is sodium dodecyl sulphate, a soap, a phospholipid or a mixture of phospholipids.

7. A process according to claim 6 wherein said soap is a sodium, potassium or ammonium stearate, oleate or palmitate.

8. A process according to claim 1 wherein the pH of the chitosan solution employed in step (b) is about 1–2.5 and the final pH of said stable emulsion is about 3.5.

9. A process according to claim 2 wherein said cross-linking electrolyte is a water soluble polyphosphate.

10. A process according to claim 9 wherein polyphosphate is a tripolyphosphate.

11. A process according to claim 2 wherein in step (c) the second agent is an organic acid and wherein said period of time is from 2 to 6 hours.

12. A process according to claim 2 wherein in step (d) the aqueous phase is removed from the dispersion obtained in (c) by lyophilization, spray-drying or oven vacuum drying.

13. A process according to claim 1 which further comprises after said step (b) the addition of a dispersing agent.

14. A process according to claim 13 wherein said dispersing agent is sodium dodecyl sulphate.

15. A UV radiation photoprotectant preparation comprising as active ingredient a UV radiation photoprotectant, an anionic emulsifier and chitosan.

16. A preparation according to claim 15 further comprising a pharmaceutically acceptable additive, carrier or diluent.

17. A preparation according to claim 15 in the form of an aqueous emulsion.

18. A preparation according to claim 17 wherein the aqueous emulsion is dried.

19. A preparation according to claim 15 wherein the UV radiation photoprotectant is octyl methoxy cinnamate.

20. A preparation according to claim 15 wherein the anionic emulsifier is a phospholipid or a mixture of phospholipids.

21. A preparation according to claim 20 wherein the anionic emulsifier is lecithin.

22. A preparation according to claim 15 wherein the active ingredient is present in the form of chitosan microcapsules.

23. A process for the microcapsulation of oil droplets dispersed in an aqueous solution comprising the steps of:
   (a) forming an oil-in-water emulsion, by homogenizing oil, water and an anionic emulsifier;
   (b) adding to the emulsion obtained in (a) an aqueous chitosan solution while continuously homogenizing the mixture; and
   (c) increasing the pH of the mixture obtained in (b) to precipitate the chitosan on the oil droplets to form microcapsules.

24. A process according to claim 23 wherein the oil is octyl methoxy cinnamate.

25. A process according to claim 23 wherein the anionic emulsifier is lecithin.

26. A sustained release or long acting preparation comprising:
   as active ingredient vitamin E or a UV radiation photoprotectant;
   an anionic emulsifier;
   chitosan;
   and optionally further comprising pharmaceutically acceptable additive, carriers or diluents.

27. A sustained-release preparation according to claim 26 in the form of an aqueous emulsion.

28. A sustained release or long acting preparation comprising:
   as active ingredient vitamin E or a UV radiation photoprotectant;
   an anionic emulsifier;
   chitosan;
   and optionally further comprising pharmaceutically acceptable additive, carriers or diluents,
   wherein said emulsion is prepared by the process according to claim 1.

29. A sustained release preparation according to claim 26 wherein said active ingredient is present in the form of chitosan microcapsules.

30. A sustained release or long acting preparation comprising:
   as active ingredient vitamin E or a UV radiation photoprotectant;
   an anionic emulsifier;
   chitosan;
   and optionally further comprising pharmaceutically acceptable additive carriers or diluents.
   wherein said emulsion is prepared by the process according to claim 2.

31. The process according to claim 6, wherein said phospholipid comprises lecithin.

32. The process according to claim 10, wherein said tripolyphosphate is selected from the group consisting of sodium tripolyphosphate and potassium tripolyphosphate.

33. The process according to claim 11, wherein said organic acid is selected from the group consisting of citric acid, lactic acid, acetic acid and fumaric acid.

* * * * *